(12) United States Patent
Biffi

(10) Patent No.: US 12,036,254 B2
(45) Date of Patent: Jul. 16, 2024

(54) **BACTERIAL STRAINS OF THE *Lactobacillus paracasei* SPECIES FOR USE, ORAL OR TOPICAL, IN THE TREATMENT OF DISORDERS OF THE FEMALE UROGENITAL TRACT**

(71) Applicant: LAC2BIOME S.R.L., Milan (IT)

(72) Inventor: Andrea Biffi, Trezzano Rosa (IT)

(73) Assignee: LAC2BIOME S.R.L., Milan (IT)

( * ) Notice: Subject to any disclaimer, the term of this patent is extended or adjusted under 35 U.S.C. 154(b) by 0 days.

(21) Appl. No.: 17/281,926

(22) PCT Filed: Oct. 25, 2019

(86) PCT No.: PCT/IB2019/059175
§ 371 (c)(1),
(2) Date: Mar. 31, 2021

(87) PCT Pub. No.: WO2020/084589
PCT Pub. Date: Apr. 30, 2020

(65) Prior Publication Data
US 2021/0379127 A1 Dec. 9, 2021

(30) Foreign Application Priority Data

Oct. 26, 2018 (IT) .................. 102018000009822

(51) Int. Cl.
*A61K 35/747* (2015.01)
(52) U.S. Cl.
CPC .................. *A61K 35/747* (2013.01)
(58) Field of Classification Search
None
See application file for complete search history.

(56) References Cited

U.S. PATENT DOCUMENTS

| 2002/0044926 | A1* | 4/2002 | Reid | A61K 35/745 424/93.45 |
| 2011/0206650 | A1 | 8/2011 | De Haen et al. | |
| 2016/0184372 | A1* | 6/2016 | Mogna | A61K 47/36 424/93.45 |

FOREIGN PATENT DOCUMENTS

| EP | 2596797 A1 | 5/2013 |
| WO | WO 2017/195182 A1 | 11/2017 |

OTHER PUBLICATIONS

Balzaretti et al., "The vaginal isolate Lactobacillus paracasei LPC-S01 (DSM26760) is suitable for oral administration", Frontiers in Microbiology, vol. 6, Article 952, pp. 1-13. (Year: 2015).*
Sabbatini et al., "*Saccharomyces cerevisiae*-based probiotic as novel anti-microbial agent for therapy of bacterial vaginosis", Virulence, vol. 9, No. 1, pp. 954-966. (Year: 2018).*
Balzaretti et al., "The vaginal isolate Lactobacillus paracasei LPC-S01 (DSM 26760) is suitable for oral administration", Frontiers in Microbiology, 2015, 6:952, DOI: 10.3389/fmicb.2015.00952.

* cited by examiner

*Primary Examiner* — Michelle F. Paguio Frising
*Assistant Examiner* — Grant C Currens
(74) *Attorney, Agent, or Firm* — James S. Keddie; Bozicevic, Field & Francis LLP

(57) ABSTRACT

The present invention regards a composition based on bacteria belonging to the *Lactobacillus paracasei* species for use in the treatment and/or in the prevention of a pathological condition of the female urogenital tract, preferably a pathological condition of the female genital tract, more preferably of the vagina, said pathological condition being caused by or related with a vaginal microbiota imbalance or for treating and/or preventing the symptoms related with said pathological condition.

14 Claims, 12 Drawing Sheets
Specification includes a Sequence Listing.

| α-diversity index |
|---|
| invSimpson |
| Simpson |
| Shannon |
| Chao1 |
| *Lactobacillus crispatus* |
| *Lactobacillus iners* |
| *Lactobacillus gasseri* |
| *Lactobacillus jensenii* |
| *Bifidobacterium* |
| *Streptococcus* |
| *Alloscardovia* |
| *Gardnerella* |
| *Lactobacillus kitasatonis* |
| *Atopobium* |
| *Corynebacterium* |
| *Blautia* |
| *Bacteroides* |
| *Haemophilus* |
| *Lactobacillus reuteri* |

Fig. 1B

| α-diversity indexes | invsimpson |
| | simpson |
| | shannon |
| | Chao |
| Community state type | |
| Visit | |
| Subject | |
| Lactobacillus crispatus | |
| Lactobacillus iners | |
| Lactobacillus gasseri | |
| Bifidobacterium | |
| Streptococcus | |
| Lactobacillus jensenii | |
| Alloscardovia | |
| Gardnerella | |
| Corynebacterium | |
| Enterococcus | |
| Escherichia/Shigella | |
| Veillonella | |
| Haemophilus | |
| Lactobacillus reuteri | |
| Atopobium | |
| Prevotella | |
| Clostridium sensu stricto | |
| Ureaplasma | |
| Anaerococcus | |
| Finegoldia | |
| → L. paracasei/rhamnosus | |

Fig. 3B

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: qS01a-F

<400> SEQUENCE: 1
tggaagagac cctgcgaa                                                 18

<210> SEQ ID NO 2
<211> LENGTH: 22
<212> TYPE: DNA
<213> ORGANISM: Artificial Sequence
<220> FEATURE:
<223> OTHER INFORMATION: qS01a-R

<400> SEQUENCE: 2
gaggttgatt cacaaaccgt gc                                            22

BACTERIAL STRAINS OF THE *Lactobacillus paracasei* SPECIES FOR USE, ORAL OR TOPICAL, IN THE TREATMENT OF DISORDERS OF THE FEMALE UROGENITAL TRACT

FIELD OF THE INVENTION

The present invention regards a composition based on bacteria and/or yeasts and/or other microorganisms for use, preferably for oral or topical use, in the treatment and/or in the prevention of a pathological condition of the female urogenital tract, preferably a pathological condition of the female genital tract, more preferably of the vagina, said pathological condition being caused by or related with a vaginal microbiota imbalance or for treating and/or preventing the symptoms related with said pathological condition.

STATE OF THE ART

Bacterial vaginosis (BV) is one of the most common diseases among women in fertile age.

BV is characterised by a deep alteration of the normal vaginal microflora where the Lactobacilli are replaced by an anaerobic mixed microflora. When a BV is in progress, the vaginal pH increases until it reaches values such not to allow the survival of the Lactobacilli. This biological context facilitates anaerobic bacteria, including *Gardnerella vaginalis*, which reach—in the vagina—concentrations up to one thousand times more than the normal ones. On the other hand, even treatments with antibiotics or chemotherapics locally or systemically, even though essential for the treatment of specific forms of vaginosis, can cause the destruction of the non-pathogenic flora, firstly the lactobacillary one, thus inducing the risk of relapses.

The female genital tract, in particular the vagina, is sterile up to birth: it starts to become colonised—during the passage in the birth canal or immediately thereafter—by various microorganisms which will constitute the endogenous microflora.

In the woman in fertile age, the vaginal microbial flora mainly consists of *Lactobacillus acidophilus*, having the distinctive trait of degrading monosaccharides, deriving from the scission of the glycogen of epithelial derivation by cellular enzymes and lactic acid with ensuing acidification of the vaginal environment.

The capacity of the lactobacilli to colonise the vaginal mucosa depends on the administration route and on the degree of adhesion to the epithelial cells. Formulations that go directly into the vagina, such as capsules, tablets, douches or gels, are capable of increasing the local content of Lactobacilli, if administered at appropriate amount. Instead, the oral formulations of lactobacilli must be capable of maintaining the viability thereof during the passage through the gut, preferably reaching to the level of the rectal canal before back-flowing and colonising the vaginal tract.

Thus, there still arises the need for qualitatively and quantitatively improving the vaginal bacterial flora and treating/preventing pathological conditions of the female urogenital tract and the symptoms related therewith.

Furthermore, there arises the need for providing compositions that allow to re-balance the vaginal bacterial flora that can be administered both through the oral route and through the topical route. In particular, the oral administration makes the administration of the composition and the dosing thereof easy and simple.

Lastly, there arises the need for compositions that are effective in the treatment of diseases, symptoms and/or disorders of the female urogenital tract, well-tolerated, without adverse effects, easy to produce and cost-effective.

Following an extensive research and development activity, the Applicant addresses and solves the aforementioned needs by providing compositions comprising at least one bacterial strain of the *Lactobacillus* genus according to what is indicated in the present description and in the attached claims.

Said compositions of the invention are effective in the treatment of diseases, symptoms and/or disorders of the female urogenital tract, well-tolerated, without adverse effects, easy to produce and cost-effective.

These and other objects which will be apparent from the detailed description that follows, are achieved by the bacterial strains, by the mixtures and by the compositions of the present invention thanks to the technical characteristics claimed in the attached claims.

SUMMARY OF THE INVENTION

A first aspect of the present invention regards a composition based on bacteria and/or yeasts and/or other microorganisms, preferably for oral or topical use, in the treatment and/or in the prevention of a pathological condition of the female urogenital tract, preferably a pathological condition of the female genital tract, more preferably of the vagina, said pathological condition being caused by or related with a vaginal microbiota imbalance or for treating and/or preventing the symptoms related with said pathological condition.

In particular, particularly effective were bacteria belonging to the genus selected from among: *Lactobacillus, Bifidobacterium, Bacillus, Propionibacterium, Streptococcus, Lactococcus, Aerococcus* and *Enterococcus*, preferably bacteria belonging to the *Lactobacillus* and/or *Bifidobacterium* genus.

As a matter of fact, the Applicant surprisingly proved that the administration, i.e. the use, preferably in oral form, of a composition based on bacteria belonging to the *Lactobacillus* and/or *Bifidobacterium* genus, in particular a probiotic composition comprising the *Lactobacillus paracasei* bacterial species, qualitatively and quantitatively improves the composition of the vaginal microbiota.

Thus, the composition of the present invention is particularly advantageous for the treatment of diseases related with a lactobacilli deficiency in the urogenital tract, preferably in the female urogenital tract.

In particular, the Applicant found that the composition of the present invention is capable of significantly reducing the levels of potential pathobionts of the vaginal ecosystem, such as for example those belonging to the *Candida, Gardnerella, Dorea, Streptococcus, Anaerococcus, Finegoldia, Prevotella, Peptoniphilus, Alloscardovia, Staphylococcus* and *Corynebacterium*, preferably of the *Gardnerella, Staphylococcus, Anaerococcus* and *Finegoldia* genus.

Further advantages of the present invention will be apparent from the detailed description that follows and from the examples which, however, are provided by way of non-limiting example.

BRIEF DESCRIPTION OF THE FIGURES

FIGS. 1A-1B show an analysis of the vaginal microbiota of healthy volunteers before the treatment with the composition of the present invention.

FIGS. 3A-3B show an analysis of the vaginal microbiota of the healthy volunteers after the treatment with the composition of the present invention.

DEFINITIONS

Figure 1A:
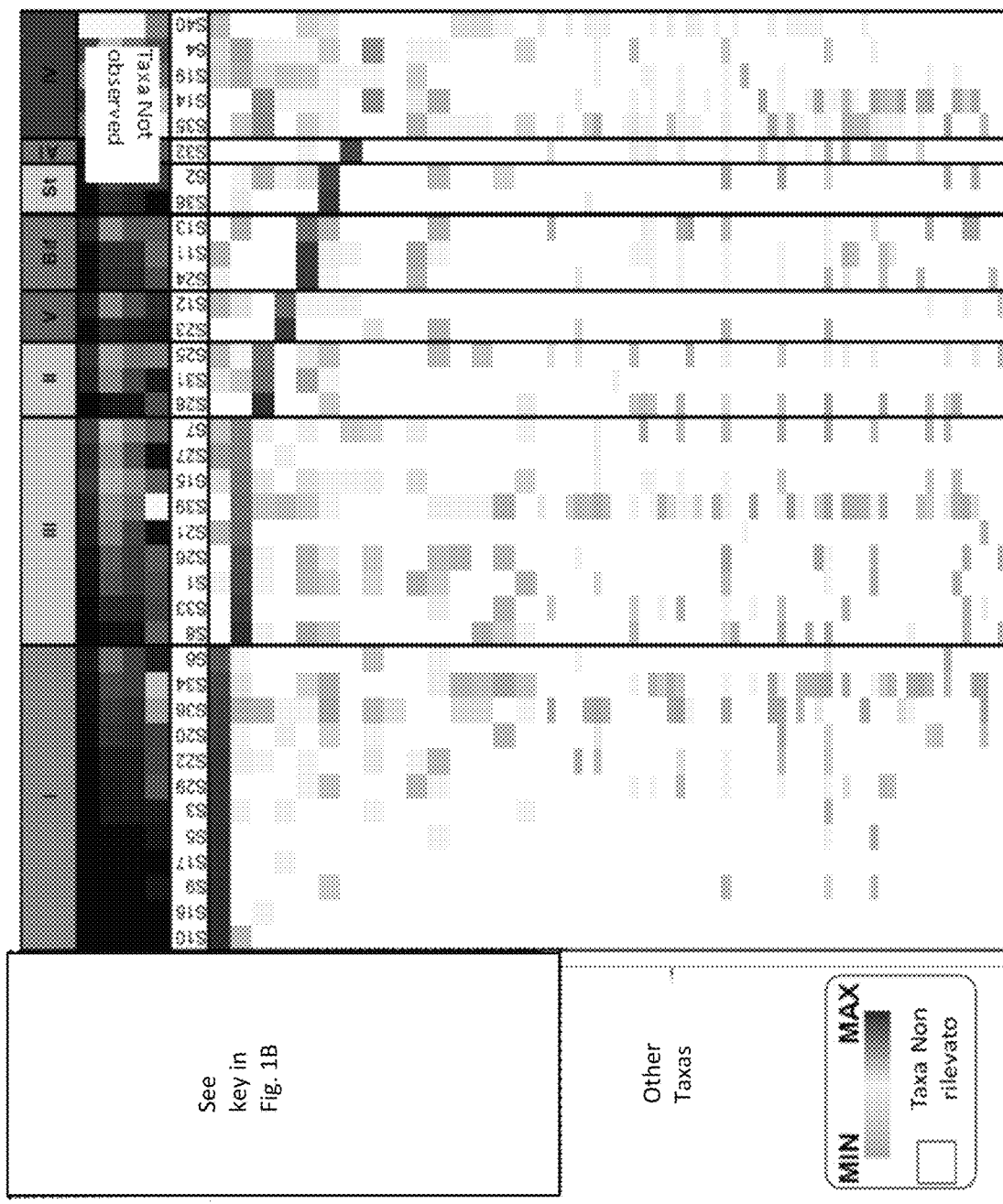

In the context of the present invention, the expression "vaginal microbiota" or "vaginal ecosystem" is used to indicate the set of microorganisms that populate the female urogenital tract, preferably the vagina, and that live balanced with respect to each other and with the vaginal environment that hosts them.

In the context of the present invention, the expression "pathobiont" is used to indicate bacteria present in the vaginal ecosystem and that are potentially pathogenic if present at high quantities.

The expression "probiotics" is used in this context to indicate the guidelines provided for by the FAO and OMS: "Live microorganisms which when administered in adequate amounts confer a health benefit on the host".

Probiotics are "microorganisms that are believed to provide health benefits when consumed", substantially quoting the definition of the two organisations mentioned above.

DETAILED DESCRIPTION

A first aspect of the present invention regards a composition based on bacteria (or bacterial strains) for use, preferably for oral or topical use, in the treatment and/or in the prevention of a pathological condition of the female urogenital tract, preferably of the female genital tract, more preferably of the vagina, said pathological condition being caused by or related with a vaginal microbiota imbalance. Furthermore, the present invention regards a composition based on bacteria for treating and/or preventing the symptoms related with said pathological condition, in needy subjects (in short composition for use of the invention or composition of the invention).

Preferably, the composition is based on probiotic bacteria as defined above, preferably said bacteria belonging to the *Lactobacillus* and/or *Bifidobacterium* genus.

Preferably, the bacteria of the *Lactobacillus* genus belong to at least one of the following species: *Lactobacillus paracasei, Lactobacillus acidophilus, Lactobacillus rhamnosus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus iners, Lactobacillus jensenii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus sakei, Lactobacillus salivarius* and *Lactobacillus sanfranciscensis*.

Preferably, the composition comprises Lactobacilli of the *L. paracasei* species, more preferably the *Lactobacillus paracasei* is the strain LPC-S01 (*Lactobacillus paracasei* LPC-S01, DSM 26760 of the DSMZ) and/or *L. casei* DG® (*Lactobacillus paracasei* CNCM 1-1572). The bacterial strain *L. casei* DG® is deposited by SOFAR S.p.A. at the National Collection of Cultures of Microorganisms of the Pasteur Institute in Paris on May 5, 1995, under deposit number CNCM 1-1572; said strain was initially named *Lactobacillus casei* DG® sub. *casei* CNCM 1-1572; it was subsequently reclassified as *Lactobacillus paracasei* DG® CNCM I-1572. It should be observed that it is still and exclusively the same bacterial strain irrespective of the name *Lactobacillus casei* DG® or *Lactobacillus paracasei* DG®.

Preferably, the composition comprises strain LPC-S01 (*Lactobacillus paracasei* LPC-S01, DSM 26760 of DSMZ) deposited at Deutsche Sammlung von Mikroorganismen und Zellkulturen GmbH (DSMZ) under access number DSM 26760 on 20 Nov. 2012 by SOFAR S.p.A.

As a matter of fact, the Applicant proved, by way of example, that strain *L. paracasei* LPC-S01, for example administered through oral route, is capable of maintaining its viability when passing through the gut, reaching the level of the rectal canal and back-flowing and colonising the vaginal tract. As a matter of fact, as extensively described in the example, the results of the metagenomic analysis of vaginal swabs and/or of faecal samples proved the presence of strain *L. paracasei* LPC-S01 in the vaginal ecosystem, proving the fact that the bacterium populated the vaginal ecosystem passing through the gut.

Preferably, the bacteria of the *Bifidobacterium* genus belong to at least one of the following species: *B. animalis, B. bifidum, B. breve, B. infantis, B. longum, B. adolescentis, B. catenulatum, B. angulatum, B. asteroides, B. bourn, B. choerinum, B. coryneforme, B. cuniculi, B. denticolens, B. dentium, B. gallicum, B. gallinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum, B. thermophilum* and *B. tsurumiense*.

Preferably said pathological condition is selected from among: infection of the female urogenital tract, preferably of the female genital tract, vaginal infection; vaginosis, preferably bacterial and/or fungal and/or caused by yeast and/or viral, more preferably candidosis, *chlamydia*, genital herpes and gonorrhoea; vaginitises, preferably atrophic; vulvodynia; alterations of the menstrual cycle, preferably hypermenorrhea, hypomenorrhea and the combinations thereof.

In a preferred embodiment of the invention, the pathological condition is caused by or related with a reduction of the levels of the Lactobacilli (bacteria of the *Lactobacillus* genus) in the vaginal ecosystem.

In a preferred embodiment of the invention, the symptoms related with said pathological condition selected from among: itchiness, redness, burning sensation, cramps, secretions, pain, dyspareunia, erythema, hypersensitivity, vaginal discharge, irritation, cervicitis, mucus and the combinations thereof.

In a preferred embodiment of the invention, said pathological condition is caused by or related with a reduction—in the vaginal ecosystem—of the levels of lactobacilli, preferably belonging to the *Lactobacillus crispatus* and/or *Lactobacillus gasseri* species. Thus, the composition of the present invention is particularly advantageous in the treatment and/or in the prevention of pathological conditions and/or of the symptoms related therewith, in subjects having a reduction or deficiency of the *L. crispatus* and/or *L. gasseri* bacteria at the level of the vaginal ecosystem.

In a further preferred embodiment of the invention, the pathological condition is caused by or related with an increased proliferation—in the vaginal ecosystem—of at least one pathobiont bacterium, preferably selected from among: *Gardnerella* genus, preferably *vaginalis* species; *Dorea* genus, preferably *D. formicigenerans* and *D. longicatena* species; *Streptococcus*, preferably *S. pyogenes, S agalactiae, S. faecalis, S. pneumoniae, S. mutans* species; *Anaerococcus*, preferably *A. hydrogenalis, A. lactolyticus, A. octavius, A. prevotii, A. tetradius, A. vaginalis* species; *Finegoldia*, preferably *F. magna* species; *Prevotella*, preferably *P. albensis, P bivia, P. brevis, P. bryantii, P. copri, P. intermedia, P. nigrescens, P. melaninogenica, P. oralis, P. oris, P. salivae* species; *Peptoniphilus*, preferably *P. asaccharolyticus, P. harei, P. coxii, P. vaginalis, P. raoultii, P. pacaensis, P. indolicus, P. ivorii, P. lacrimalis* species; *Alloscardovia*, preferably *omnicolens* species; *Staphylococcus*, preferably *Staphylococcus aureus, Staphylococcus auricularis, Staphylococcus capitis, Staphylococcus caprae, Staphylococcus cohnii, Staphylococcus delphini, Staphylococcus epidermidis, Staphylococcus haemolyticus, Staphylococcus hominis, Staphylococcus hyicus, Staphylococcus intermedius, Staphylococcus lugdunensis, Staphylococcus pseudintermedius, Staphylococcus saprophyticus, Staphylococcus warneri, Staphylococcus xylosus*, and *Corynebacterium* species, preferably *Corynebacterium diphtheriae, Corynebacterium vaginale, Corynebacterium fascians, Corynebacterium piogens, Corynebacterium simplex, Corynebacterium malli, Corynebacterium ulcerans, Corynebacterium pseudotuberculosis* (or *Corynebacterium ovis*), *Corynebacterium pyogenes, Corynebacterium haemolyticum, Corynebacterium glutamicum, Corynebacterium aquaticum, Corynebacterium pseudodiptheriticum* (or *Corynebacterium hofmannii*), *Corynebacterium urealyticum* (corynebacteria of group D2), *Corynebacterium equi, Corynebacterium bovis, Corynebacterium xerosis, Corynebacterium amycolatum, Corynebacterium jeikeiun* (corynebacteria of group JK), *Corynebacterium striatum, Corynebacterium tenuis, Corynebacterium glucoronolyticum* species and the combinations thereof. In a further embodiment of the invention, said pathological condition is simultaneously caused by or related with a reduction—in the vaginal ecosystem—of the levels of lactobacilli, preferably belonging to the *Lactobacillus crispatus* and/or *Lactobacillus gasseri* species and caused by or related with an increased proliferation—in the vaginal ecosystem—of at least one pathobiont bacterium, preferably selected from among pathobiont bacteria belonging to the genera or species mentioned above.

According to a preferred embodiment of the present invention, the composition for use, preferably for oral or topical use, as described above, preferably comprising a bacterial strain selected from among *L. paracasei* LPC-S01 (DSM 26760), *L. casei* DG® (CNCM I-1572) and the mixtures thereof, further comprises bacteria and/or yeasts and/or fungi and/or other microorganisms, considered alone or combined.

The yeasts are preferably of the *Saccharomyces* genus, more preferably of the *Saccharomyces cerevisiae* and/or *Saccharomyces boulardii* species.

Generally, the microorganisms comprised in the composition of the present invention are single or combined microorganisms of any microbial species indicated in the EFSA QPS list.

The microorganisms of the composition of the present invention are preferably live or dead and thus the composition, in the case of live microorganisms, can also be defined a probiotic, while in the case of dead microorganisms can also be defined a paraproboitic.

Alternatively, the microorganisms of the composition are in form of lysate or extract and thus the composition can also be defined as a paraproboitic.

In an alternative embodiment, the composition further comprises the metabolic bioproducts generated by the microorganisms defined as postbiotics and/or any other bacterial-related product.

Thus, the composition of the present invention is also a probiotic or a paraproboitic or a postbiotic, known or presumed.

The bacteria in the composition can be considered alone or combined variously.

Preferably, the bacteria comprised in the composition, preferably *L. paracasei* LPC-S01 (DSM 26760), *L. casei* DG® (CNCM 1-1572) and the mixtures thereof, are capable of surviving the gastrointestinal transit and reaching the gut live and viable; then, preferably, the bacteria comprised in the composition are potentially capable of reaching the vaginal ecosystem, preferably through the rectal canal, live.

According to an aspect of the present invention, said composition, preferably comprising a bacterial strain selected from among *L. paracasei* LPC-S01 (DSM 26760), *L. casei* DG® (CNCM I-1572) and the mixtures thereof, comprises an amount (concentration) of bacteria variable from 1 billion to 100 billion, preferably 2-70 billion, more preferably 2-60 billion, more preferably 3-55 billion of bacterial cells for each administration (or dose), more preferably 20-30 billion of bacterial cells for each administration (or dose).

Preferably, the administration occurs at least 1-2 times per day. The administration may occur through any route. The composition of the invention may be formulated for administration through gastroenteric rote, such as oral, sublingual or buccal route, or formulated for topical administration, such as transmucosal, rectal, cutaneous or vaginal administration.

Preferably, the administration of the composition is through the oral route, more preferably in form of tablets, capsules, bars, granular powder, gelcaps, oral soluble granules, sachets, pills or drinkable vials.

Alternatively, the composition of the invention is formulated in a form capable of carrying out an action through topical route, for example as powder for gynaecological suspensions, vaginal ovules, vaginal tablets and/or capsules, vaginal douches, vaginal gels, vaginal creams or enema.

Alternatively, the composition of the invention is formulated as liquid, for example as syrup or as beverage, or it is added to a food product, for example a yoghurt, a cheese, a fruit juice.

In an embodiment of the invention, the composition, preferably comprising a bacterial strain selected from among *L. paracasei* LPC-S01 (DSM 26760), *L. casei* DG® (CNCM I-1572) and the mixtures thereof, further comprises excipients generally accepted for the production of probiotic and/or pharmaceutical and/or food products. In the context of the present invention, the excipients acceptable for pharmaceutical or food purposes comprise all auxiliary substances known to the man skilled in the art for the preparation of compositions in solid, semi-solid or liquid form such as, for example, diluents, solvents (including water, glycerine, ethyl alcohol), solubilisers, acidifiers, thickeners, sweeteners, flavour enhancers, colouring agents, lubricants, surfactants, preservatives, pH stabilising buffers and the mixtures thereof.

In a further embodiment of the invention, the composition of the invention, preferably comprising a bacterial strain selected from among *L. paracasei* LPC-S01 (DSM 26760), *L. casei* DG® (CNCM I-1572) and the mixtures thereof, can be enriched with vitamins, oligo-elements, preferably zinc and selenium, enzymes, prebiotic substances such as fructo-oligosaccharides (FOS), galacto-oligosaccharides (GOS), inulin, guar gum, botanicals (i.e., plant extracts), soy isoflavones or the combinations thereof.

Preferably, for the medical uses described above, the composition can be administered, through oral or topical route, once per day, or twice per day.

In a preferred embodiment, the composition is administered in a single administration or several daily administrations, continuously or whenever needed.

A further aspect of the present invention regards a method for the curative and/or preventive treatment of a pathological condition of the female urogenital tract or related symptoms, preferably of the female genital tract, more preferably of the vagina, said pathological condition being caused by or related with a vaginal microbiota imbalance, wherein said administration provides for the administration of an effective amount of the composition of the invention, preferably comprising a bacterial strain selected from among *L. paracasei* LPC-S01 (DSM 26760), *L. casei* DG® (CNCM I-1572) and the mixtures thereof, to a needy subject.

The composition for use of the invention, preferably comprising a bacterial strain selected from among *L. paracasei* LPC-S01 (DSM 26760), *L. casei* DG® (CNCM I-1572) and the mixtures thereof, can be a pharmaceutical composition (or Live Biotherapeutic Products), a medical device composition, a dietary supplement or a food product or a composition for a food for special medical purposes or a probiotic product, preferably a nutraceutical food product.

In the context of the present invention, the expression "medical device" is used in the meaning according to the Italian Legislative Decree no 46 dated 24 Feb. 1997 or according to the new Medical Device Regulation (EU) 2017/745 (MDR).

In the context of the present invention, the expression "subjects" is used to indicate human subjects or animal subjects (e.g. pets, such as dogs or cats or other mammals). Preferably, the compositions of the invention are for use in treatment methods for human subjects.

Unless specified otherwise, the expression composition or mixture or other comprising a component at an amount "comprised in a range from x to y" is used to indicate that said component can be present in the composition or mixture or other at all the amounts present in said range, even though not specified, extremes of the range comprised.

Embodiments (FRnr) of the present invention are indicated below:

FR1. A composition comprising bacteria, preferably probiotics, belonging to the *Lactobacillus* and/or *Bifidobacterium* genus for use in the treatment and/or in the prevention of a pathological condition of the female urogenital tract, preferably a pathological condition of the female genital tract, more preferably of the vagina, said pathological condition being caused by or related with a vaginal microbiota imbalance or for treating and/or preventing the symptoms related with said pathological condition.

FR2. Composition for use according to FR1, wherein said pathological condition is selected from among: infection of the female urogenital tract, preferably of the female genital tract, more preferably vaginal infection; vaginosis, preferably bacterial and/or fungal and/or related with yeasts and/or viral; candidosis, *chlamydia*, genital herpes, gonorrhoea; vaginitis, preferably atrophic; vulvodynia; alterations of the menstrual cycle, preferably hypermenorrhea, hypomenorrhea and the combinations thereof.

FR3. Composition for use according to FR1 or FR2, wherein said symptoms related with said pathological condition are selected from among: itchiness, redness, burning sensation, cramps, secretions, pain, dyspareunia, erythema, hypersensitivity, vaginal discharge, irritation, cervicitis, mucus and the combinations thereof.

FR4. Composition for use according to any one of FR1-FR3, wherein said pathological condition is related with, or dependent on: 1) a reduction—in the vaginal ecosystem—of the levels of bacteria of the *Lactobacillus* genus, preferably the bacteria belonging to the *Lactobacillus crispatus* and/or *Lactobacillus gasseri* species, and/or 2) an increase of the proliferation—in the vaginal ecosystem—of at least one microorganism selected from among: *Gardnerella* genus, preferably *vaginalis* genus; *Dorea* genus, preferably *D. formicigenerans* and *D. longicatena* species, *Streptococcus*, preferably *S. pyogenes, S agalactiae, S. faecalis, S. pneumoniae, S. mutans* species: *Anaerococcus*, preferably *A. hydrogenalis, A. lactolyticus, A. octavius, A. prevotii, A. tetradius, A. vaginalis* species; *Finegoldia*, preferably *F. magna* species; *Prevotella*, preferably *P. albensis, P bivia, P. brevis, P. bryantii, P. copri, P. intermedia, P. nigrescens, P. melaninogenica, P. oralis, P. oris, P. salivae* species; *Peptoniphilus*, preferably *P. asaccharolyticus, P. harei, P. coxii, P. vaginalis, P. raoultii, P. pacaensis, P. indolicus, P. ivorii, P. lacrimalis* species; *Alloscardovia*, preferably *omnicolens* species, *Staphylococcus*, preferably *Staphylococcus aureus, Staphylococcus auricularis, Staphylococcus capitis, Staphylococcus caprae, Staphylococcus cohnii, Staphylococcus delphini, Staphylococcus epidermidis, Staphylococcus haemolyticus, Staphylococcus hominis, Staphylococcus hyicus, Staphylococcus intermedius, Staphylococcus lugdunensis, Staphylococcus pseudintermedius, Staphylococcus saprophyticus, Staphylococcus warneri, Staphylococcus xylosus* species and *Corynebacterium*, preferably *Corynebacterium diphtheriae, Corynebacterium vaginale, Corynebacterium fascians, Corynebacterium piogenes, Corynebacterium simplex, Corynebacterium malli, Corynebacterium ulcerans, Corynebacterium pseudotuberculosis* (or

*Corynebacterium ovis*), *Corynebacterium pyogenes, Corynebacterium haemolyticum, Corynebacterium glutamicum, Corynebacterium aquaticum, Corynebacterium pseudodiptheriticum* (or *Corynebacterium hofmannii*), *Corynebacterium urealyticum* (corynebacteria of group D2), *Corynebacterium equi, Corynebacterium bovis, Corynebacterium xerosis, Corynebacterium amycolatum, Corynebacterium jeikeiun* (corynebacteria of group JK), *Corynebacterium striatum, Corynebacterium tenuis, Corynebacterium glucoronolyticum* species and the combinations thereof.

FR5. Composition for use according to any one of FR1-FR4, wherein the bacteria of the *Lactobacillus* genus belong to at least one of the following species: *Lactobacillus paracasei, Lactobacillus acidophilus, Lactobacillus rhamnosus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus iners, Lactobacillus jensenii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus sakei, Lactobacillus salivarius, Lactobacillus sanfranciscensis* and the combinations thereof.

FR6. Composition for use according to any one of FR1-FR5, wherein the bacteria of the *Lactobacillus* genus are of the *paracasei* species, strain LPC-S01 (DSM 26760 of the DSMZ) and/or *casei* species, strain DG® (*Lactobacillus paracasei* CNCM 11572).

FR7. Composition for use according to any one of FR1-FR6, wherein the bacteria of the *Bifidobacterium* genus belong to at least one of the following species *B. animalis, B. bifidum, B. breve, B. infantis, B. longum, B. adolescentis, B. catenulatum, B. angulatum, B. asteroides, B. boum, B. choerinum, B. coryneforme, B. cuniculi, B. denticolens, B. dentium, B. gallicum, B. gallinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum, B. thermophilum, B. tsurumiense* and the combinations thereof.

FR8. Composition for use according to any one of FR1-FR7, wherein said composition further comprises: bacteria, yeasts, fungi and/or further microorganisms.

FR9. Composition for use according to any one of FR1-FR8, wherein said yeast belongs to the *Saccharomyces* genus, preferably to the *Saccharomyces cerevisiae* and/or *Saccharomyces boulardii* species.

FR10. Composition for use according to any one of FR1-FR9, wherein the bacteria are live or dead, in form of lysate or extract, or in form of postbiotics.

FR11. Composition for use according to any one of claims FR1-FR10, wherein the bacteria are at an amount comprised in the range from 1 billion to 100 billion, preferably 2-60 billion, more preferably 2-50 billion, more preferably 3-55 billion bacterial cells for each administration, more preferably 20-30 billion bacterial cells for each administration.

FR12. Composition for use according to any one of FR1-FR11 formulated for oral use, preferably in form of tablets, capsules, bars, granular powder, gelcaps, oral soluble granules, sachets, pills or drinkable vials; or formulated in a form capable of carrying out an action through topical route, preferably such as powder for gynaecological suspensions, vaginal ovules, vaginal tablets and/or capsules, vaginal douches, vaginal gels, vaginal creams or enema; or formulated as liquid, preferably as syrup or as beverage; or it is added to a food product, preferably to a yoghurt, a cheese, a fruit juice.

FR13. Composition for use according to any one of FR1-FR12, where said composition is administered at least 1-2 times per day.

FR14. Composition for use according to any one of FR1-FR13 combined with amino acids, supplements, vitamins, oligo-elements, preferably zinc and/or selenium, enzymes and/or prebiotic substances, preferably fructo-oligosaccharides (FOS), galacto-oligosaccharides (GOS), inulin, guar gum, botanicals (i.e., plant extracts), soy isoflavones or the combinations thereof.

FR15. Use of a composition comprising bacteria, preferably probiotics, belonging to the *Lactobacillus* and/or *Bifidobacterium* genus, for: 1) increasing the levels or increasing the proliferation of bacteria of the *Lactobacillus crispatus* and/or *Lactobacillus gasseri* species and/or 2) form reducing the levels or reducing the proliferation of at least one microorganism selected from among: *Gardnerella* genus, preferably *vaginalis* species; *Dorea* genus, preferably *D. formicigenerans* and *D. longicatena* species, *Streptococcus*, preferably *S. pyogenes, S agalactiae, S. faecalis, S. pneumoniae, S. mutans* species; *Anaerococcus*, preferably *A. hydrogenalis, A. lactolyticus, A. octavius, A. prevotii, A. tetradius, A. vaginalis* species; *Finegoldia*, preferably *F. magna* species; *Prevotella*, preferably *P. albensis, P bivia, P. brevis, P. bryantii, P. copri, P. intermedia, P. nigrescens, P. melaninogenica, P. oralis, P. oris, P. salivae* species; *Peptoniphilus*, preferably *P. asaccharolyticus, P. harei, P. coxii, P. vaginalis, P. raoultii, P. pacaensis, P. indolicus, P. ivorii, P. lacrimalis* species; *Alloscardovia*, preferably *omnicolens* species; *Staphylococcus*, preferably *Staphylococcus aureus, Staphylococcus auricularis, Staphylococcus capitis, Staphylococcus caprae, Staphylococcus cohnii, Staphylococcus delphini, Staphylococcus epidermidis, Staphylococcus haemolyticus, Staphylococcus hominis, Staphylococcus hyicus, Staphylococcus intermedius, Staphylococcus lugdunensis, Staphylococcus pseudintermedius, Staphylococcus saprophyticus, Staphylococcus warneri, Staphylococcus xylosus*, and *Corynebacterium* species, preferably *Corynebacterium diphtheriae, Corynebacterium vaginale, Corynebacterium fascians, Corynebacterium piogens, Corynebacterium simplex, Corynebacterium malli, Corynebacterium ulcerans, Corynebacterium pseudotuberculosis* (or *Corynebacterium ovis*), *Corynebacterium pyogenes, Corynebacterium haemolyticum, Corynebacterium glutamicum, Corynebacterium aquaticum, Corynebacterium pseudodiptheriticum* (or *Corynebacterium hofmannii*), *Corynebacterium urealyticum* (corynebacteria of group D2), *Corynebacterium equi, Corynebacterium bovis, Corynebacterium xerosis, Corynebacterium amycolatum, Corynebacterium jeikeiun* (corynebacteria of group JK), *Corynebacterium striatum, Corynebacte-*

*rium tenuis, Corynebacterium glucoronolyticum* species and the combinations thereof.

Example

In this context, it was experimentally proven—by means of a randomised, double blind, crossover clinical study controlled towards placebo—that strain *L. paracasei* LPC-S01 (DSM 26760), administered through oral route with the composition subject of the present invention (in short, study composition):

Is capable of reaching—at vaginal level—in live form;
It qualitatively and quantitatively modifies the composition of the vaginal microbiota.

*Lactobacillus paracasei* LPC-S01 (DMS 26760) is a bacterial strain originally isolated from the vaginal mucosa of healthy adult women, which proved to have characteristics compatible with the use thereof as intestinal probiotic, as the capacity to resist against in vivo gastrointestinal transit, adhere to the in vitro intestinal epithelium and reduce the activation of NF-κB in presence of inflammatory stimulation in the polarised Caco-2 intestinal epithelial cells (Balzaretti et al., 2015).

The trial envisaged the following steps:
Pre-recruitment step (4 weeks) wherein healthy volunteers followed their conventional diet with prohibition to take: probiotic fermented milk (thus, conventional yoghurt was allowed), probiotic dietary supplements, prebiotic dietary supplements;
At the end of this pre-recruitment period, the volunteers were randomised to receive 1 capsule of PREGYN® (Sofar, Trezzano Rosa, Italy) per day, or of a placebo not containing microorganisms, for 4 weeks;
PREGYN® consists of capsules containing 24 billion of CFUs (colony-forming units) of *Lactobacillus paracasei* LPC-S01 (DSM 26760). The placebo consisted of capsules identical to those of the probiotic. The taste and the colour of the active substance and of the placebo were identical
The product was administered under starving conditions in the morning, at least 10 minutes before breakfast or, if forgotten, in the evening, before going to bed and 2 hours after the last meal in any case.
Following the first 4 weeks of treatment, the volunteers were subjected to 4 weeks of identical wash-outs at the pre-recruitment period.
At the end of the wash-out period, the volunteers took 1 capsule of PREGYN® or of placebo per day for 4 weeks according to the cross-over design.

The trial protocol was approved by the Research Ethics Committee of Sacco hospital, Università degli Studi di Milano (opinion no 0019288, 24 Jul. 2015).

Inclusion Criteria
Healthy adult women, aged between 18 and 45 years, with an 18.5≤BMI≤25
Written informed consent of the patient Exclusion Criteria
The presence of any of the following criteria led to the exclusion of the volunteers from the trial:
Urogenital infections in the previous 3 months, especially bacterial vaginosis
Urogenital abnormalities
Women with acknowledged or planned pregnancy or breastfeeding women
Taking antibiotics and/or probiotics in the month prior to the start of the experimentation
Therapy with steroids, rapid pass blood glucocorticoids such as beclomethasone dipropionate or budesonide, through systemic or topical route, in progress or within the month prior to recruitment;
Chronic inflammatory bowel diseases;
Intestinal diseases of infectious, actinic, endocrine origin or caused by or related with drugs (microscopic colitis);
Immunodeficiency;
Volunteers with malignant neoplasms of any type, or with previous neoplasm history (patients with anamnesis of other malignant neoplasms which were removed surgically and who did not reveal relapses within five years prior to the inclusion in the trial can thus be recruited);
Renal, hepatic, hematologic, heart, lung, neurological, psychiatric, immunological, gastrointestinal or endocrine diseases, if they are clinically significant;
Any serious disease that could interfere with the treatment;
Recent history or suspicion of abuse of alcohol or substances;
Presence of dementia of any type or other possible causes of progressive deterioration of mental capacity or psycho-physical incapacity which reduces the capacity to take the therapy subject of prescription
Inadequate reliability or presence of conditions that can determine a non-compliance/failure of the volunteer to join the protocol
Previous participation to this trial Recruitment of the Volunteers and Study Design
Each volunteer was initially instructed on the entire procedure to follow, which envisaged a total of 5 meetings for each volunteer after about 14 days from the end of menstruations of the subject.

During the first meeting, the informed consent and personal data of the volunteer were collected.

Furthermore, the volunteer received general information regarding the implementation of the trial and was informed on diet changes to be carried out in the subsequent 4 pre-recruitment weeks (prohibition to take the previously indicated products). Lastly, the volunteer filled out this questionnaire regarding the eating habits and sexual life thereof and received a special diary to be filled out daily up to the end of the trial.

After 4 weeks, the volunteer went the second meeting with a faecal sample thereof (sample TO, visit V1), collected during the 24 previous hours in a special container which was handed thereto at the previous meeting. For optimal preservation, the faecal samples were preserved at ambient temperature and delivered to the laboratory within 24 hours. Furthermore, a vaginal swab was conducted and blood was drawn. At the second meeting, the volunteer was given the probiotic product (or a placebo) to be taken during the 4 subsequent weeks. Lastly, the volunteer was instructed on how to take the product and filled out the same questionnaires on the eating habits and on the sexual life filled out at the first meeting.

At the end of the 4 weeks of taking the product (or the placebo), the volunteer went to the third meeting with another faecal sample (T1, visit V2) collected during the previous 24 hours and another vaginal swab was conducted and more blood was drawn. At the third meeting, the volunteer filled out a questionnaire regarding possible effects, both positive and adverse, related with the consumption of the product. The volunteer was then instructed on the subsequent 4 weeks, during which once again the volunteer could not take the previously mentioned products and filled out the same questionnaires of the previous meetings.

At the end of these 4 weeks, the volunteer went to the fourth meeting with a faecal sample thereof (T2, visit V3), a vaginal swab was conducted and blood was drawn and she received the probiotic product (or placebo) to be taken during the 4 subsequent weeks. Lastly, the volunteer filled out the same questionnaires of the previous meetings.

Lastly, after 4 weeks taking the product (or the placebo), the volunteer went to the fifth meeting to hand over the final faecal sample (T3, visit V4) and to conduct the final vaginal swab and blood-drawing. During this final meeting, the volunteer filled out a questionnaire similar to the one given at the third meeting. Furthermore, during this visit the volunteer also filled out the same eating habits and sexual life questionnaires and returned the diary.

Information on the volunteers' diet during the previous weeks was collected at each visit. 40 volunteers, 24 of whom completed the trial according to the described protocol (60% compliance) were recruited to the trial.

Methods and Materials

Capsules of Probiotic Product and Placebo

The probiotic product (composition according to the invention) consists in a gelatine capsule containing at least 24 billion viable cells of bacterial strain *L. paracasei* LPC-S01 (DSM 26760).

Said capsules contain silicon dioxide and magnesium stearate as anti-caking agents and coloured externally with titanium dioxide.

The placebo consists of capsules identical—in terms of colour and shape—to the probiotic product.

Vaginal Sample Collection and Total DNA Extraction

Vaginal swabs were collected at visits V1, V2, V3 e V4 (Table 1), transferred in 750 µl of PowerBead solution (Qiagen GmbH, Hilden, Germany) and preserved at −80° C. until they were processed for DNA extraction. Furthermore, during visits V1 to V4, the volunteers handed over a faecal sample collected during the previous 24 hours in a special container which had been given to them at visit V0. The faecal samples were also preserved at −80° C. until they were processed for DNA extraction, as follows.

The vaginal swabs in the PowerBead solution were thawed in ice. The swabs were squeezed several times rotating on the inner wall of the sampling tube to release the entire amount of buffer solution or vaginal mucus adhered to the vaginal swab under aseptic conditions (subsequent swabs were used for isolating the target probiotic strain). The samples were then processed using the DNeasy® PowerLyzer® PowerSoil® Kit (Qiagen GmbH) with a slight change consisting in incubating the samples in PowerBead solution at 65° C. for 10 minutes after adding solution C1. The mechanical lysis of the cells was conducted using a Bead Beater Precellys 24 (Bertin Technologies, Montigny le Bretonneux, France). A similar procedure was followed for the extraction of DNA from faecal samples. In particular, after thawing in ice, the samples were vigorously mixed for 2-3 minutes using a sterile spatula. The samples were weighed (250 mg) in a PowerBead test tube and the DNA was extracted as mentioned above. The DNA obtained from both the vaginal or faecal samples were quantified using Take3 Micro-Volume, analysed in a microplate reader using the Gen5 software (BioTek Instruments, Inc., Winooski, VT, USA), diluted to 10 ng/µl and preserved at −80° C. up to use.

All faecal and vaginal samples collected at the experimental centre were preserved at −80° C. up to before being subjected to microbiota analysis. Specifically, the faecal and vaginal microbiota were analysed through the nucleotide sequence analysis of portions of the encoding gene for the 16S rRNA bacterial ribosomal subunit and for the presence of strain *L. paracasei* LPC-S01. More specifically, a metagenomic strategy consisting in the following steps was adopted:

extraction, quantification and normalisation of the metagenomic DNA of the samples;

PCR amplification of the hypervariable regions V3 of the 16S rRNA encoding bacterial gene;

quantification of the products of PCR;

sequencing using the fusion primer technique of Ion Torrent (single reads of 200 bp; Life Technologies);

Bioinformatics analysis of the sequences (characterisation of the microbial communities, hierarchical clustering, taxonomic analysis, construction of phylogenetic dendrograms using heatmaps).

Quantification of *L. paracasei* LPC-S01 in Vaginal and Faecal Samples Using Quantitative PCR Probiotic strain *L. paracasei* LPC-S01 (DSM 26760) in both vaginal and faecal samples was quantified using quantitative PCR (qPCR) with qS01a-F (5'TGGAAGA-GACCCTGCGAA-3') and qS01a-R (5' GAGGTTGATT-CACAAACCGTGC-3'), strain-specific primers targeting a theoretical encoding sequence of the proteins in the genome project of strain LPC-S01 (Balzaretti et al., 2015). Furthermore, the total number of bacteria was quantified using 357F-907R panbacterial primers intended for region V3-V5 of gene 16S rRNA (Muyzer et al., 1993). The qPCR was amplified in a final volume of 15 µl containing 7.5 µl of EvaGreen® Supermix (Bio-Rad Laboratories S.r.l., Segrate, Italy), 0.5 µM each primer and 50 ng of metagenomic DNA from vaginal or faecal samples. Amplification was conducted using the following conditions: initially maintaining at 95° C. for 3 minutes and 39 cycles at 95° C. for 30 seconds, 58° C. for 30 seconds and 72° C. for 30 seconds. The fusion curves were analysed using Bio-Rad CFX Manager 3.1 to confirm the specificity of the amplification products. A standard calibration curve for quantifying the LPC-S01 cells was prepared by mixing different numbers of LPC-S01 cells in vaginal swabs. To this end, numerous samples of vaginal swab were collected from the volunteers and transferred in 750 ml of PowerBead solution. The swab samples were combined in a test tube, mixed vigorously and equally distributed in seven test tubes. After the quantification of *L. paracasei* LPC-S01 using a C6 Plus BD Accuri™ flow cytometry (BD Biosciences, San Jose, California, USA), probiotic cells were added to each swab sample (from 101 to 106 cells), except for one used as a control sample without adding bacterial cells; then, the DNA was extracted as described above. Similarly, a standard calibration curve for quantifying the probiotic strain in faecal samples was prepared as described above (Arioli et al., 2018). Furthermore, the standard calibration curve for quantifying the total bacterial cells in the vaginal swab sample was prepared by creating a pool of vaginal swabs. To this end, vaginal swab sample were handed over by healthy volunteers in 750 ml of PowerBead solution and mixed. Then, the pool of vaginal swabs was correctly mixed and concentrated through centrifugation. After determining the total concentration of the bacterial cells through flow cytometry, the concentrated buffer was diluted in series and each dilution was subjected to DNA extraction following the aforementioned procedures. The DNA obtained from various previous dilutions of the pool of vaginal swabs was subsequently used for the quantitative PCR to generate a standard calibration curve for estimating the total bacterial cells in the vaginal swab sample and of the trial.

Quantification of *Gardnerella vaginalis* in Vaginal Swabs Through QPCR

The presence of cells of *G. vaginalis* in the vaginal swabs was established using qPCR with specific-species primers targeting the lactate dehydrogenase gene.

Isolation of *L. paracasei* LPC-S01 from Vaginal Swabs

After the aseptic processing for total extraction of DNA, the vaginal swabs were transferred to the Man-Rogosa-Sharpe (MRS) (pH 6.5) broth supplemented with ribose (1% p/v), vancomycin (1 μg/ml) and kanamycin (10 μg/ml) (rvkMRS) for the semi-selective isolation of the probiotic strain. The inoculated broth test tubes containing the swab were incubated at 37° C. for 48 hours under anaerobic conditions (Anaerocult A, Merck KGaA, Darmstadt, Germany). The culture broths were used for extracting the DNA and qPCR with specific primers for LPC-S01 as described above. Each culture broth was simultaneously spread on agar medium (agar rvkMRS). The randomly selected colonies were examined under the microscope to establish the morphology thereof and they were identified by the colony PCR (Arioli et al., 2018).

The metadata was filed in the European Nucleotide Archive (ENA) of the European bioinformatics institute under adhesion number PRJEB30833.

Statistical Analysis

Statistically significant changes in the relative abundance of bacterial taxa were determined through the signed rank Wilcoxon test for the data paired using the Benjamini-Hochberg correction (Haynes, 2013) when necessary. Correlation analysis with the relative abundance of faecal and vaginal taxa were conducted using the Kendall and Spearman formulae. Significance was set at P≤0.05; significance in the 0.05<P<0.10 interval was accepted as trend. In order to find links between the probiotic treatment and changes in the relative bacterial abundance, the LMM (Linear Mixed Model) algorithm supervised by automatic learning was adopted using the "lmer" function in the "lme4" library (Bates et al., 2015) in R statistical software (version 3.4.2). The MM adaptation was tested using the Akaike Information Criterion (AIC).

Study Design

The trial envisages 5 visits according to Table 1:

TABLE 1

| | pre-recruitment | treatment 1 | wash-out | treatment 2 |
|---|---|---|---|---|
| | 4 settimane | 4 settimane | 4 settimane | 4 settimane |
| Visit | T0 | T1 | T2 | T3 |
| Vaginal swab/ Collecting faecal sample | 1 | 2 | 3 | 4 |

Proliferation of the RRNA 16S Gene of Vaginal and Faecal Samples

The DNA extracted from faecal samples and vaginal swabs was analysed at the Institute for Genome Sciences (University of Maryland, School of Medicine, Baltimore, MD, USA) through the proliferation of the 16S rRNA gene with the Illumina HiSeq 2500 rapid run sequencing of the variable region V3-V4. The total number of generated reads amounted to 6,470,846 for 215 total samples with an average of 30,097 reads per sample. The total number of reads filtered amounted to 5,501,139 and out of these, 5,099,077 reads were combined. In particular, the number of combined reads per sample amounted to 13,340±8,677 (mean±standard deviation) (max-min 11,594-4,570) and 34,387±9,376 (34,125-22,393) for the vaginal and faecal DNA, respectively. The 16S rRNA gene profiling data for analysing faecal and vaginal microbiota was analysed using the R statistical software (version 3.1.2) with a DADA2 software package (Callahan et al., 2016) associated with the speciateIT taxonomic assignment tool.

As concerns region V3-V4, DADA2 used a read cut-off after 255 nt and above and 225 nt in inverse reads. Taxonomic assignment was conducted on the SILVA database according to the personalised pipeline available on GitHub free of charge (github.com/Ravel-Laboratory/speciateIT). The α-diversity (Chao1, Simpson, invSimpson and Shannon) and β-diversity index analysis were conducted using the R software to describe the intra and inter-subjective diversity, respectively. The vaginal microbiota stratification in community state types was conducted based on the relative abundance of the most representative taxon in the sample, using 50% of the total reads per sample as limit. If no taxon in a sample exceeds the 50% abundance, that sample is assigned to the community state types (CST) IV.

Results

Statistical analysis was conducted considering the stratification samples of community state types (CST), with the aim of considering samples that, even though smaller in number, can be more homogeneous in terms of taxonomic composition.

Composition of the vaginal microbiota of the baseline volunteers (T0, visit V1).

Figure 2:
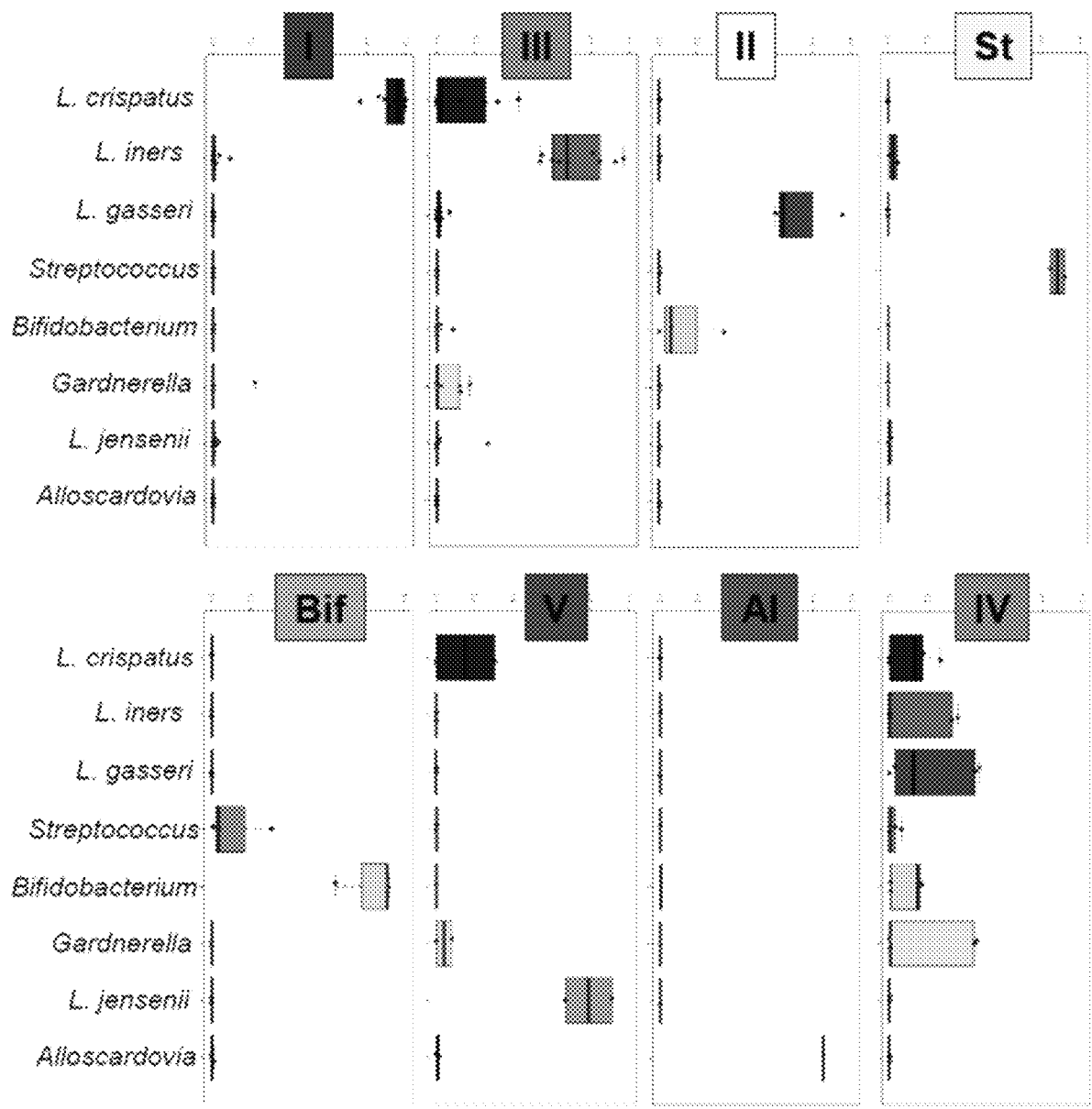
FIG. 2 shows a recapitulatory chart of the most significant microorganisms in the composition of the vaginal microbiota of the healthy volunteers before the treatment with the composition of the present invention.

After the taxonomic assignment of the sequencing reads, a total of 69 bacterial taxa (average of 17 and median of 15 taxa per sample) was found. Such analysis revealed significant differences for CST I (*L. crispatus*-dominant), which was the most common among the women subject of trial (n=10) (FIGS. 1A, 1B, and 2). As a matter of fact, the most dominant bacteria were *Lactobacillus crispatus* and *Lactobacillus iners*, detected in 68% of the subjects, followed by the members of the *Finegoldia* (65%), *Streptococcus* (65%) and *Bifidobacterium* (62%) genera. All other taxa were found in less than 50% of the subjects.

Safety and tolerability.

No serious adverse event was observed during the trial.

Composition of the vaginal microbiota of the volunteers after treatment.

In order to establish whether the oral administration of a strain of *L. paracasei* LPC-S01 had changed the composition of the vaginal microbiota of the subjects under study, we used the rRNA 16S gene profiling to analyse four vaginal swabs per subject collected from women who did not complete the trial according to the protocol (n=24). In particular, the vaginal bacterial community was immediately characterised before and after the steps of administering the composition according to the invention (or placebo), according to the crossover design represented in table 1.

In particular, there was observed significant reduction of potential pathobionts such as *Staphylococcus* (P=0.022), *Finegoldia* (P=0.022) and *Anaerococcus* (P=0.036), all of which were related with bacterial vaginosis (Table 2A).

Figure 3A:
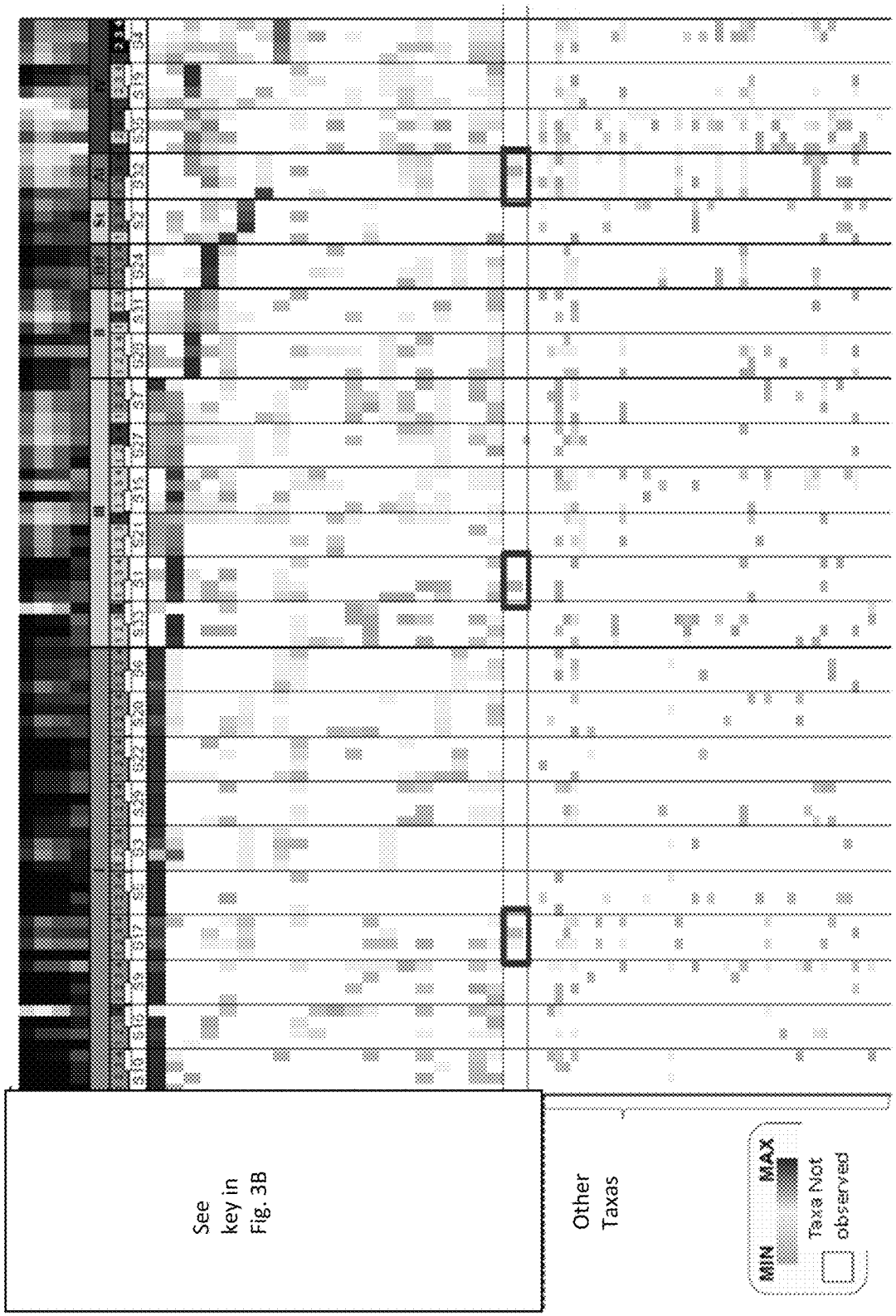

As concerns CST I, there was observed an increase trend as regards *L. crispatus* (P=0.064) species and a decrease trend for the other two *Prevotella* (P=0.059) and *Peptoniphilus* (P=0.059) pathobionts (Table 2A) (FIGS. 3A and 3B).

Lastly, there was observed significant changes on the bacterial taxa on taking probiotics when considering the CST eubiotics I, II (*L. gasseri*-dominant) and "Bif" (*Bifidobacterium*-dominant) together (n=13).

In particular, after the period of taking probiotics (T1, visit V2), there was observed a significant increase of *L. crispatus* (P=0.027) and reduction of *Anaerococco* (P=0.036), alongside a decrease trend as pertains to *Finegoldia* (P=0.067) and *Staphylococcus* (P=0.097).

On the contrary, there was only observed an increase trend for the *Bifidobacterium* (P=0.059) genus with respect to the placebo taking step for the same group of subjects (Table 2B).

TABLE 2A

| Genus | *L. paracasei* LPC-S01 | | Placebo | |
|---|---|---|---|---|
| | P value | Trend | P value | trend |
| Staphylococcus | 0.022 | decrease | n.s. | / |
| Finegoldia | 0.022 | decrease | n.s. | / |
| Anaerococcus | 0.036 | decrease | n.s. | / |
| Prevotella | 0.059 | decrease | n.s. | / |
| Peptoniphilus | 0.059 | decrease | n.s. | / |
| L. crispatus | 0.064 | increase | n.s. | / |

TABLE 2B

| Genus | *L. paracasei* LPC-S01 | | Placebo | |
|---|---|---|---|---|
| | P value | Trend | P value | trend |
| L. crispatus | 0.026 | increase | n.s. | / |
| Anaerococcus | 0.036 | decrease | n.s. | / |
| Finegoldia | 0.066 | decrease | n.s. | / |
| Staphylococcus | 0.097 | decrease | n.s. | / |
| Bifidobacterium | n.s. | / | 0.059 | increase |

On the contrary, no significant changes were observed in any specific taxon for the other CSTs, plausibly due to the vast variability in the taxonomic composition between the samples and/or the limited number of subjects in each group.

Figure 5A:
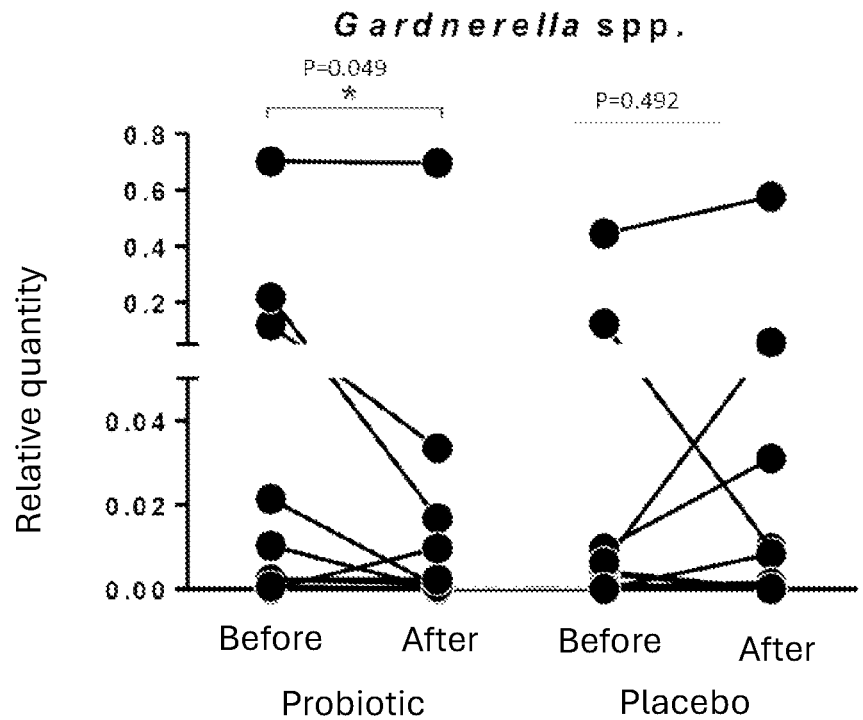
FIG. 5A shows the quantification of the levels of *Gardnerella* spp in the healthy volunteers before and after the treatment with the composition of the present invention or after treatment with the placebo; the statistically significant differences are based on the Wilcoxon signed-rank test.
Figure 5B:
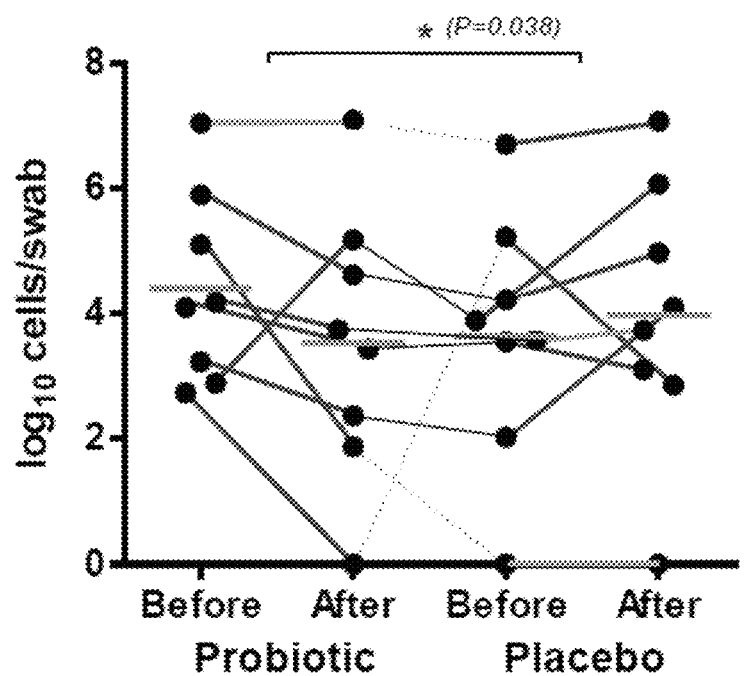
FIG. 5B shows the absolute qPCR quantification of the *Gardnerella* cells in the vaginal swabs.
Figure 6A:
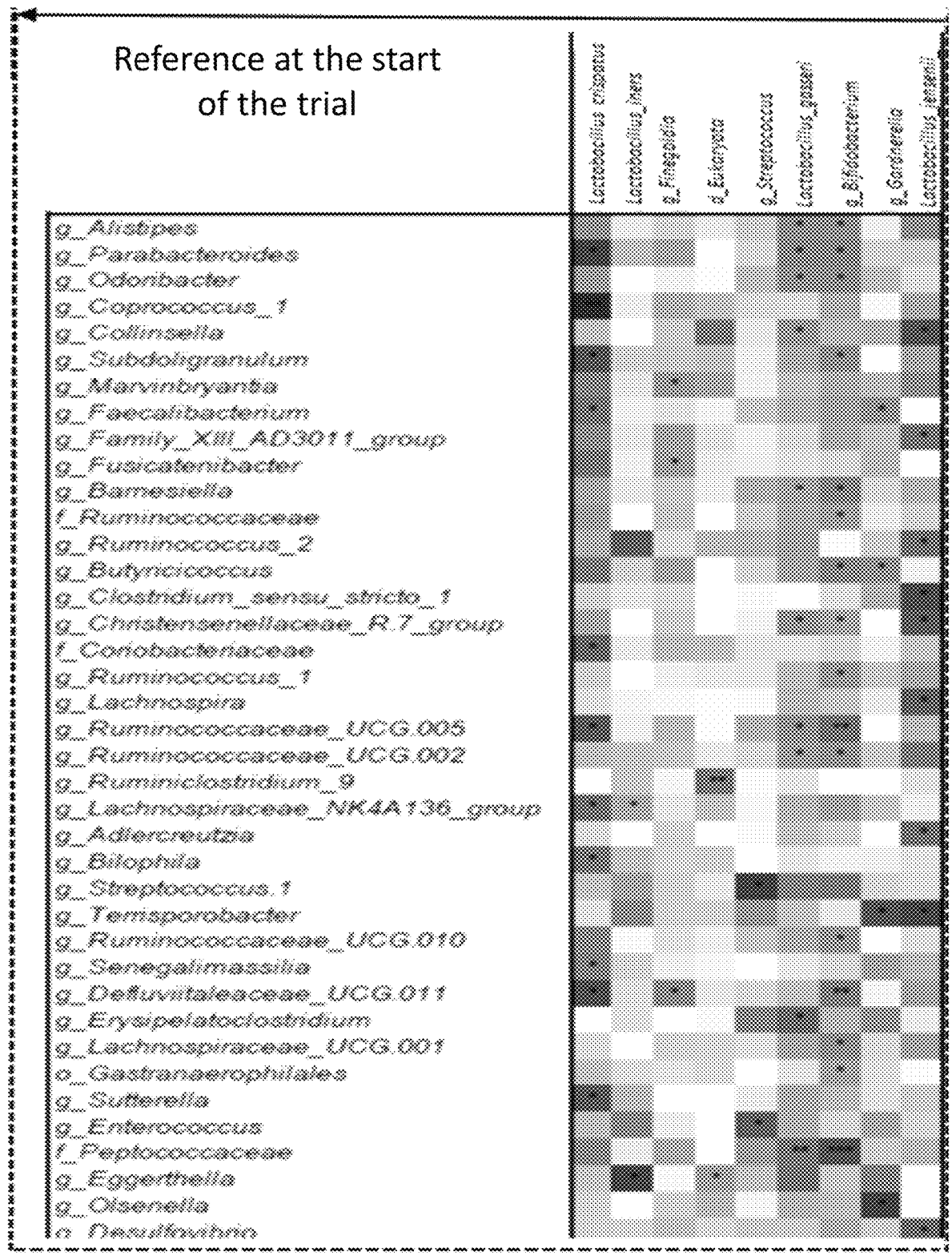
FIGS. 6A-6C show a correlation between the microorganisms of the vaginal and intestinal microbiota of the healthy volunteers before, during and after the treatment with the composition of the present invention.
Figure 6B:
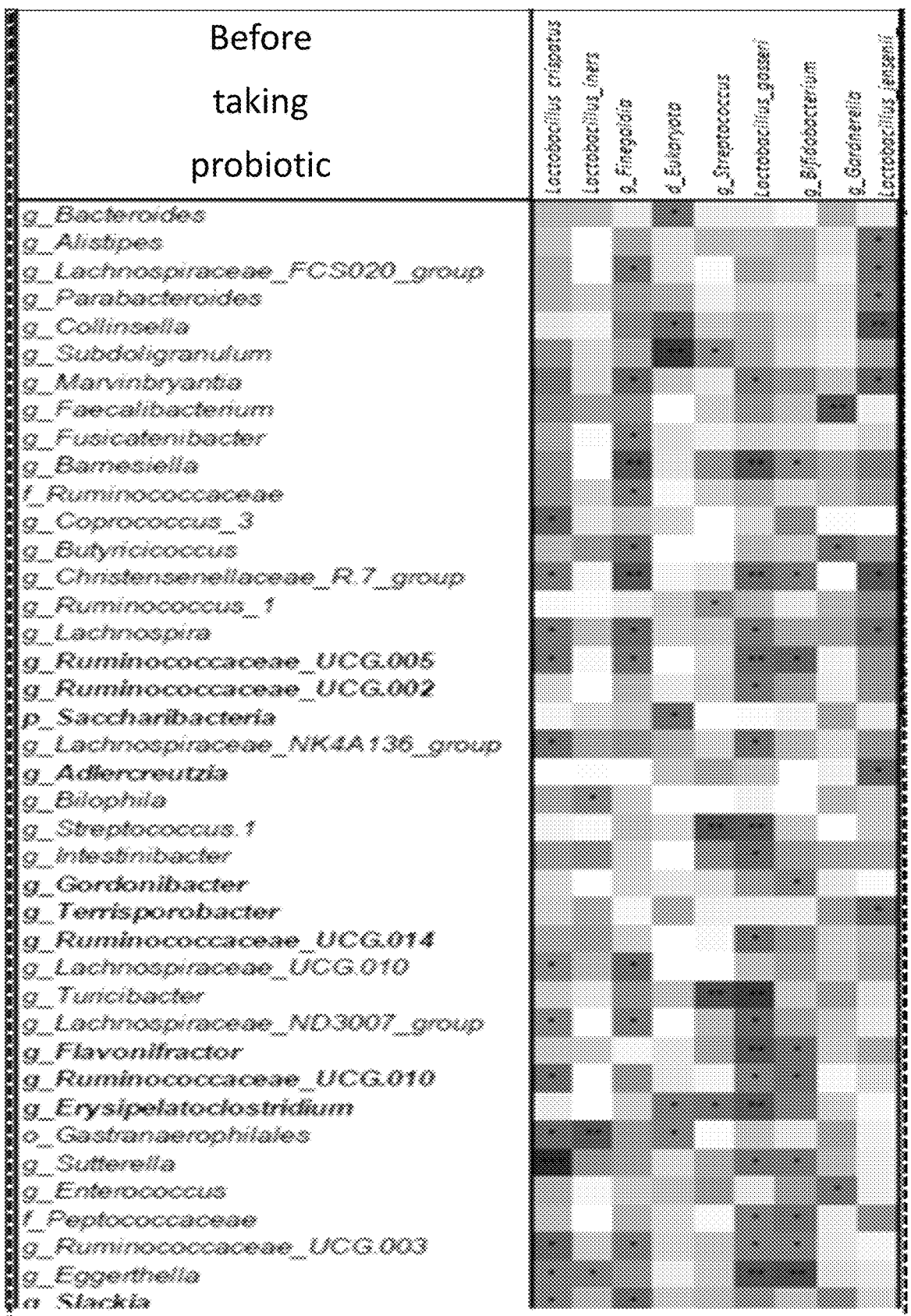
Figure 6C:
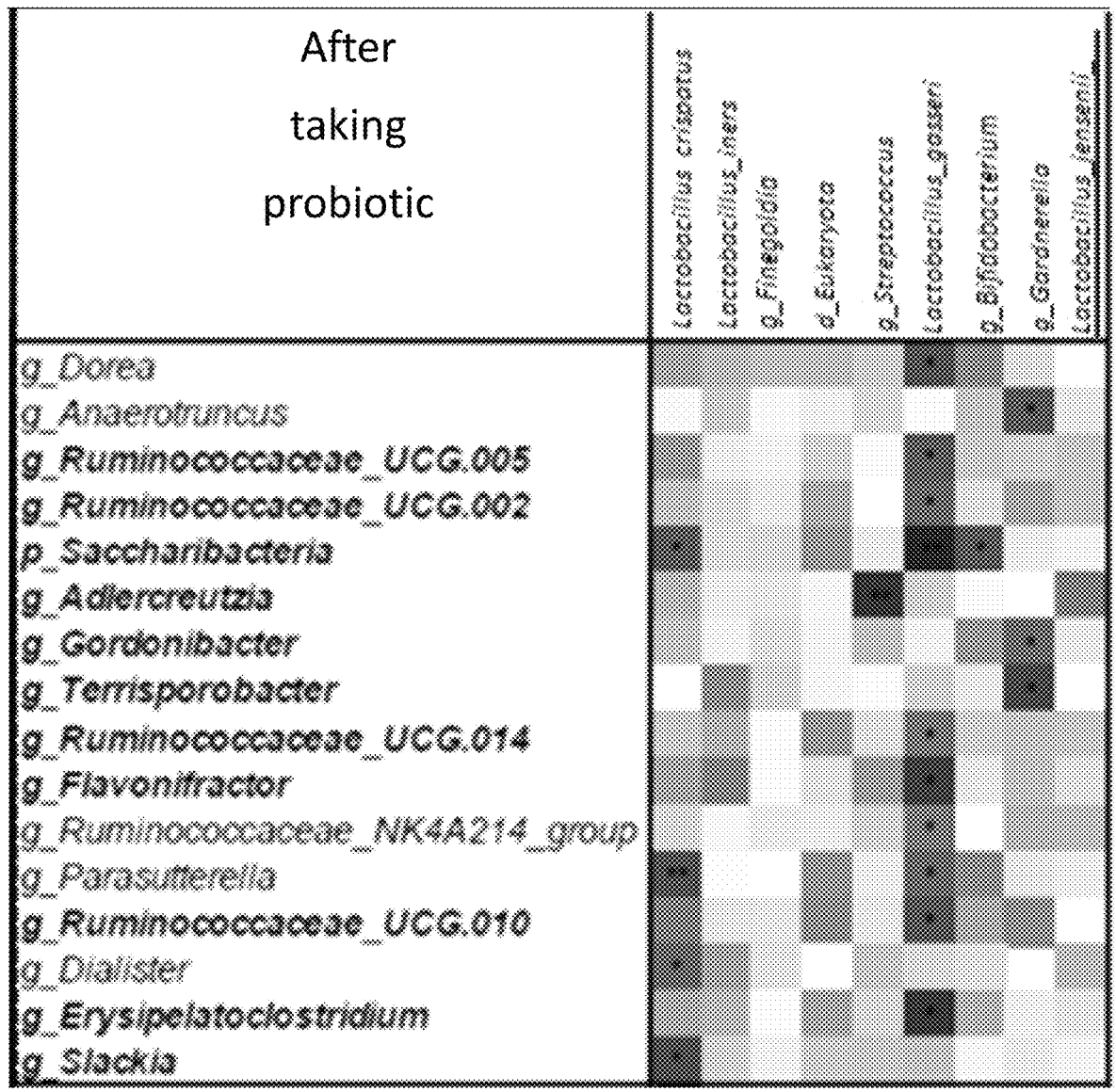
Figure 7A:
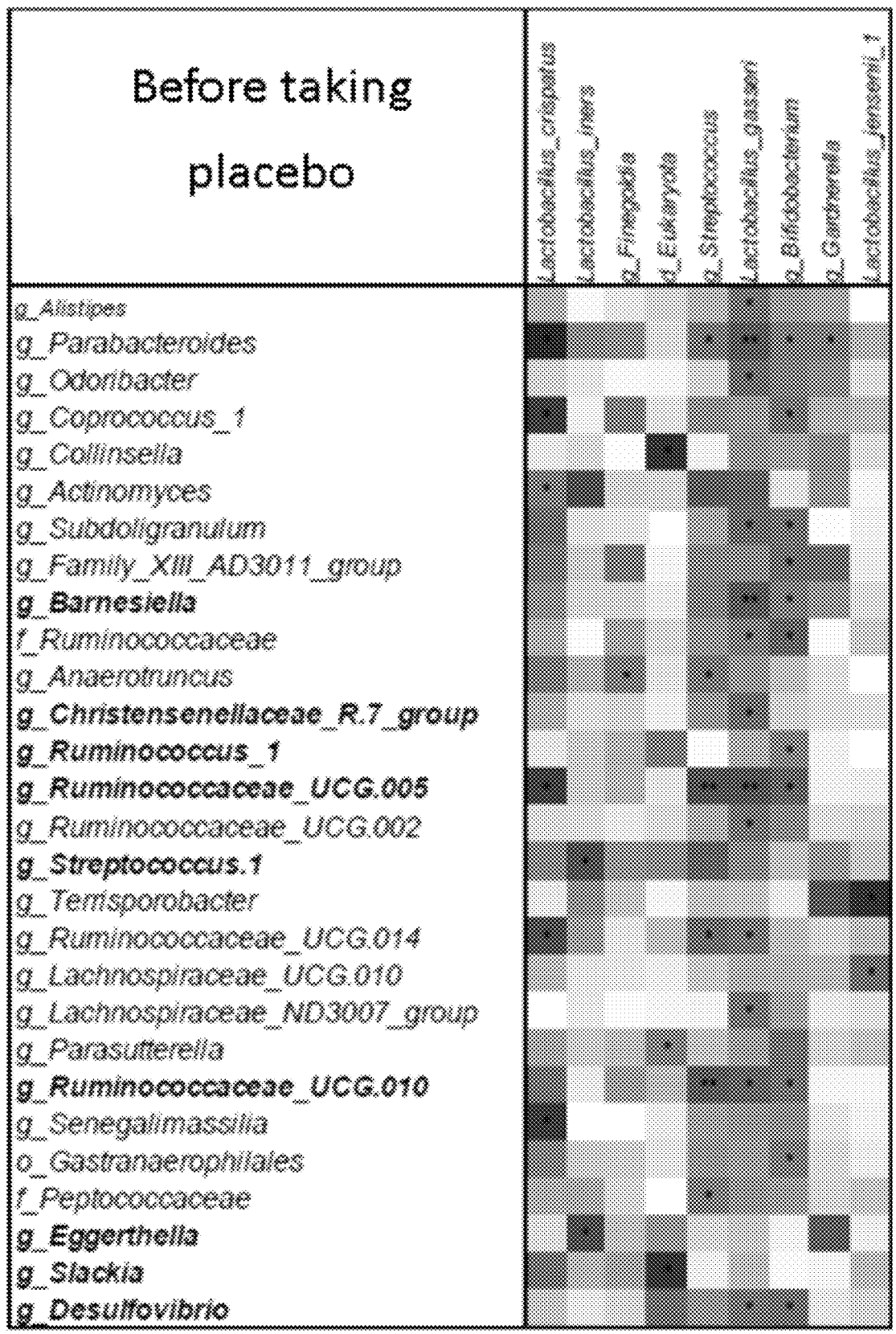
FIGS. 7A-7B show a correlation between the microorganisms of the vaginal and intestinal microbiota of the healthy volunteers before and after treatment with the placebo.
Figure 7B:
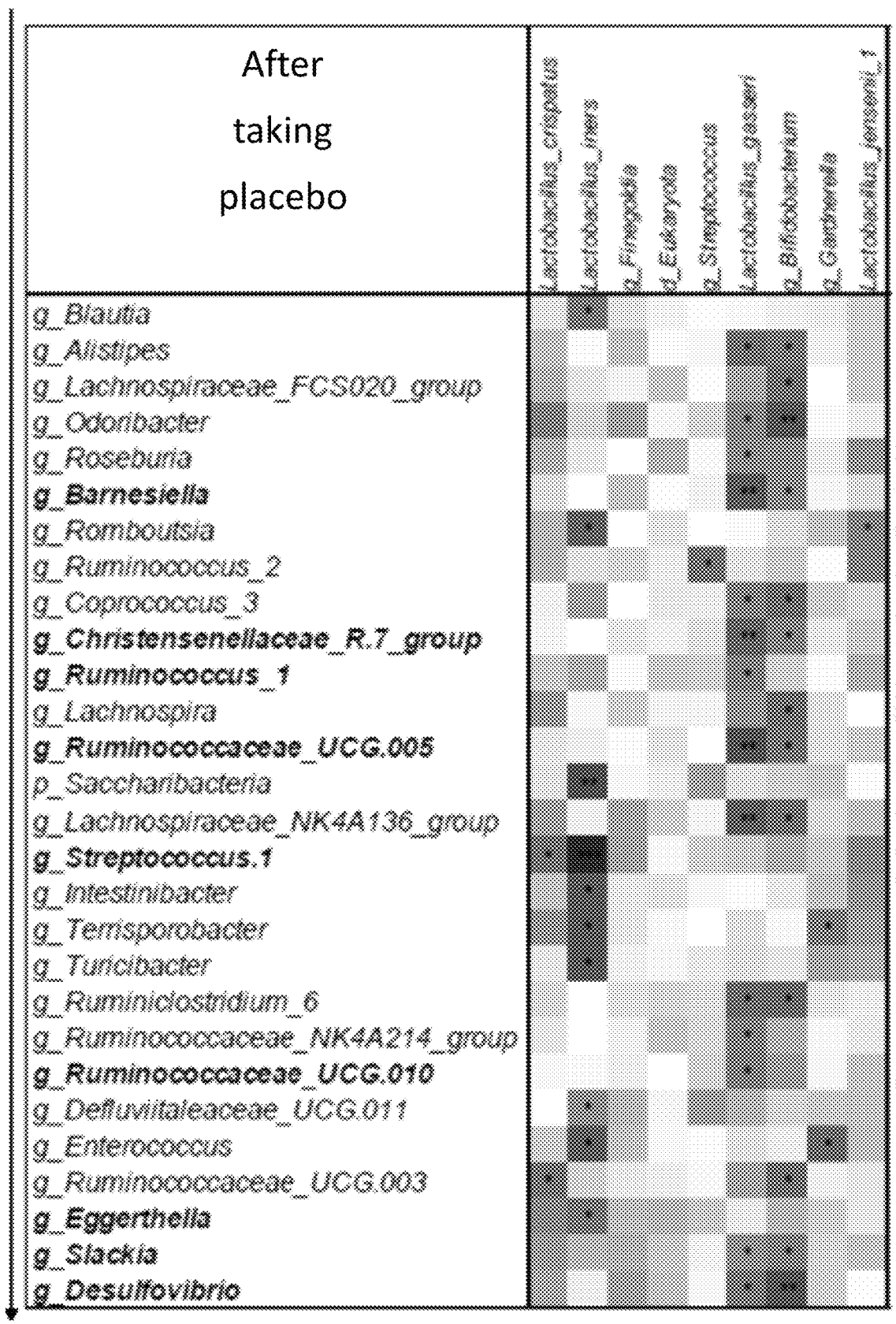

The possibility of evaluating the impact of oral administration of probiotics on the relative abundance of specific bacterial taxa in the vaginal microbiota was strongly limited by the strong stratification of the structure of the vaginal bacterial community and by the relatively low number of volunteers who completed the trial per protocol (n=24). Thus, statistical analysis were conducted through the "Wilcoxon signed-rank" test as concerns taxas that were present in at least 30% of the samples (arbitrary limit). The Wilcoxon signed-rank test revealed the significant reduction of the relative abundance of the *Gardnerella* genus (P=0.0496) after the period of administration of LPC-S01 (FIG. 5.*a*). Considering the pathogenic nature of *Gardnerella vaginalis*, these results suggest a potential positive effect of the composition subject of study on the vaginal microbial ecosystem. The significant reduction of the abundance of *Gardnerella vaginalis* during the administration of the composition of the invention was also observed with qPCR experiments, which were conducted on DNA extracted from vaginal swabs using specific primers for *G. vaginalis* (FIG. 5.*b*).

Figure 4:
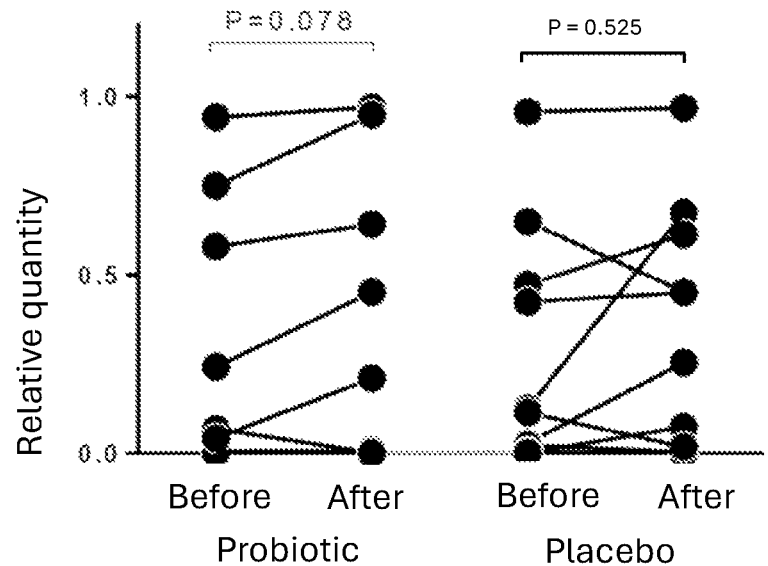
FIG. 4 shows the quantification of the levels of *Lactobacillus gasseri* in the healthy volunteers before and after the treatment with the composition of the present invention or after treatment with the placebo; the statistically significant differences are based on the Wilcoxon signed-rank test.

Furthermore, there was observed an increase trend of the *Lactobacillus gasseri* species (P=0.078) (FIG. 4).

Recovery of the *L. paracasei* LPC-S01 strain from the vaginas of the volunteers The 16S rRNA gene profile of the vaginal swabs revealed the presence of reads taxonomically assigned to group *L. paracasei/L. ramnosus* in 3 subjects (subjects S1, S17 and S23). In particular, said reads appeared in these three volunteers after the administration of the composition of the inventio; thus, it was theorised that these results are a consequence of the migration of strain *L. paracasei* LPC-S01 from the intestine to the vaginal mucosa. In order to verify this theory, a qPCR analysis was conducted with specific primers for strain *L. paracasei* LPC-S01 using the DNA isolated from all vaginal swabs collected during the trial. According to the rRNA 16S gene profiling, significant amplifications were obtained only for subjects S1 (for the swab collected at visit V2) and S17 (for the swab collected at visits V2 and V3) but not for subject S32. Furthermore, strain *L. paracasei* LPC-S01 was isolated on rvkMRS plates from the swabs of subject S17 only. Furthermore, specific qPCR tests were conducted per strain to quantify strain *L. paracasei* LPC-S01 in faecal samples. LPC-S01 was exclusively observed in faecal samples collected at the end of the period of administration of probiotics from 21 out of 23 subjects under study, at a concentration comprised between 5.6 and 8.1 log 10 cells per gram of faeces.

Overall, these results prove that strain *L. paracasei* LPC-S01 migrated and temporarily colonised the vaginal mucosa of a percentage of healthy women who ingested this bacterium.

CONCLUSIONS

The administration of PREGYN® (composition according to the invention) is thus capable of re-balancing the vaginal microbiota, increasing the concentrations of Lactobacilli, such as *Lactobacillus crispatus*, important for preventing a high proliferation of microorganisms potentially pathogenic for the vaginal ecosystem.

*L. paracasei* LPC-S01 was observed in the vaginal swab samples of two out of three subjects subject of analysis treated with the composition of the invention, suggesting that the colonisation of *L. paracasei* LPC-S01 taken through oral route in the vagina is possible, even though limited.

Furthermore, PREGYN® (composition according to the invention) is important for the reduction of the levels of the potentially pathogenic microorganisms, such as *Gardnerella, Dorea, Streptococcus, Anaerococcus, Finegoldia, Prevotella, Peptoniphilus, Alloscardovia, Staphylococcus* and *Corynebacterium*, preferably of *Gardnerella, Staphylococcus, Anaerococcus* and *Finegoldia*.

In conclusion, this trial confirms that the vaginal microbiota of healthy Italian Caucasian women in reproductive age can be stratified in the same community structures described previously for other populations. Furthermore, the CST dominated by *L. crispatus* was confirmed as the most common among Caucasian women in reproductive age, followed by CST dominated by *L. iners*. Lastly, this trial shows that the vaginal bacterial ecosystem of healthy women is quite stable; however, the oral administration of bacterial strain *L. paracasei* LPC-S01 can affect the relative abundance of specific taxas such as *Gardnerella vaginalis*. This discovery suggests a potential positive impact of the oral administration of bacterial strain *L. paracasei* LPC-S01 on the vaginal microbial ecosystem.

The invention claimed is:

1. A method of increasing *Lactobacillus crispatus* and *Lactobacillus gasseri* in the urogenital tract of a female patient having symptoms of a urogenital condition and reduced *L. crispatus* and *L. gasseri* in said urogenital tract, said method comprising:
   administering *Lactobacillus paracasei* LPC-S01 to said female patient, thereby increasing *L. crispatus* and *L. gasseri* in said urogenital tract,
   wherein said *L. paracasei* LPC-S01 is deposited at Deutsche Sammlung von Mikroorganismen und Zellkulturen GmbH (DSM) under accession number DSM 26760.

2. The method according to claim 1, wherein said urogenital condition is a pathological condition of the female genital tract.

3. The method according to claim 1, wherein said urogenital condition is selected from the group consisting of infection of the female urogenital tract, vaginosis, candidiasis, *chlamydia*, genital herpes, gonorrhea, vaginitis, vulvodynia, alterations of the menstrual cycle, and combinations thereof.

4. The method according to claim 1, wherein said symptoms of a urogenital condition are selected from the group consisting of itchiness, redness, burning sensation, cramps, secretions, pain, dyspareunia, erythema, a hypersensitivity, vaginal discharge, irritation, cervicitis, mucus, and combinations thereof.

5. The method according to claim 1, wherein the urogenital tract of the female also has an increase in at least one microorganism belonging to a genus selected from the group consisting of *Gardnerella, Dorea, Streptococcus, Anaerococcus, Finegoldia, Prevotella, Alloscardovia, Staphylococcus*, and *Corynebacterium*.

6. The method according to claim 5, wherein the urogenital tract of the female also has increase in at least one microorganism belonging to a species selected from *Gardnerella vaginalis, Dorea formicigenerans, D. longicatena, Streptococcus pyogenes, S agalactiae, S. faecalis, S. pneumoniae, S. mutans, Anaerococcus hydrogenalis, A. lactolyticus, A. octavius, A. prevotii, A. tetradius, A. vaginalis, Finegoldia magna, Prevotella albensis, P bivia, P. brevis, P. bryantii, P. copri, P. intermedia, P. nigrescens, P. melaninogenica, P. oralis, P. oris, P. salivae, Peptoniphilus, P. asaccharolyticus, P. harei, P. coxii, P. vaginalis, P. raoultii, P. pacaensis, P. indolicus, P. ivorii, P. lacrimalis, Alloscardovia omnicolens, Staphylococcus aureus, Staphylococcus auricularis, Staphylococcus capitis, Staphylococcus caprae, Staphylococcus cohnii, Staphylococcus delphini, Staphylococcus epidermidis, Staphylococcus haemolyticus, Staphylococcus hominis, Staphylococcus hyicus, Staphylococcus intermedius, Staphylococcus lugdunensis, Staphylococcus pseudintermedius, Staphylococcus saprophyticus, Staphylococcus warneri, Staphylococcus xylosus, Corynebacterium diphtheriae, Corynebacterium vaginale, Corynebacterium fascians, Corynebacterium piogens, Corynebacterium simplex, Corynebacterium malli, Corynebacterium ulcerans, Corynebacterium pseudotuberculosis* (or *Corynebacterium ovis*), *Corynebacterium pyogenes, Corynebacterium haemolyticum, Corynebacterium glutamicum, Corynebacterium aquaticum, Corynebacterium pseudodiptheriticum* (or *Corynebacterium hofmannii*), *Corynebacterium urealyticum* (corynebacteria of group D2), *Corynebacterium equi, Corynebacterium bovis, Corynebacterium xerosis, Corynebacterium amycolatum, Corynebacterium jeikeiun* (corynebacteria of group JK), *Corynebacterium striatum, Corynebacterium tenuis*, and *Corynebacterium glucoronolyticum*.

7. The method according to claim 1, wherein said composition further comprises: at least one bacterium, at least one yeast, at least one fungus and/or at least one microorganism.

8. The method according to claim 7, wherein said at least one yeast belongs to the *Saccharomyces* genus.

9. The method according to claim 1, wherein said *L. paracasei* LPC-S01 is live, dead, in the form of a lysate, in the form of a bacterial extract, or in the form of a postbiotic.

10. The method according to claim 1, wherein said composition comprises said *L. paracasei* LPC-S01 in an amount of 1 billion to 100 billion bacterial cells per dose.

11. The method according to claim 1, wherein said composition is formulated for oral use.

12. The method according to claim 11, wherein said composition is in solid form of tablets, capsules, bars, granular powder, gelcaps, mouth-soluble granules, sachets or pills; or formulated as liquid; or added to a food product, said composition being for oral use.

13. The method according to claim 1, wherein said composition is formulated in a form capable of carrying out an action through topical route.

14. The method according to claim 1, wherein said composition is formulated for topical use and is in the form of a powder for gynecological suspensions, vaginal ovule, vaginal tablet and/or capsule, vaginal douche, vaginal gel, vaginal cream, or enema.

* * * * *